United States Patent
Sarr et al.

(10) Patent No.: US 8,082,793 B2
(45) Date of Patent: Dec. 27, 2011

(54) ADJUSTABLE PROBE FOR ULTRASONIC TESTING

(75) Inventors: Dennis P. Sarr, Kent, WA (US); Hien T. Bui, Kent, WA (US)

(73) Assignee: The Boeing Company, Chicago, IL (US)

( * ) Notice: Subject to any disclaimer, the term of this patent is extended or adjusted under 35 U.S.C. 154(b) by 556 days.

(21) Appl. No.: 12/252,714

(22) Filed: Oct. 16, 2008

(65) Prior Publication Data

US 2010/0095775 A1 Apr. 22, 2010

(51) Int. Cl.
*G01N 29/26* (2006.01)
(52) U.S. Cl. .................. 73/621; 73/634; 73/640
(58) Field of Classification Search .......... 73/618, 73/620, 621, 634, 640
See application file for complete search history.

(56) References Cited

U.S. PATENT DOCUMENTS

| | | | |
|---|---|---|---|
| 4,807,476 A | 2/1989 | Cook et al. | |
| 6,161,436 A * | 12/2000 | McLean, Jr. | 73/632 |
| 6,658,939 B2 | 12/2003 | Georgeson et al. | |
| 7,617,732 B2 * | 11/2009 | Bui et al. | 73/618 |
| 7,644,618 B2 * | 1/2010 | Fetzer et al. | 73/632 |
| 7,690,259 B2 * | 4/2010 | Bui et al. | 73/625 |
| 7,836,768 B2 * | 11/2010 | Young et al. | 73/620 |

OTHER PUBLICATIONS

U.S. Appl. No. 12/038,670, filed Feb. 27, 2008.

* cited by examiner

*Primary Examiner* — J M Saint Surin

(57) ABSTRACT

A system for performing ultrasonic testing on a composite part includes an ultrasonic transducer, a shoe for holding the transducer, and means for automatically adjusting position of the transducer during ultrasonic testing. The transducer position is adjusted to account for geometry variations in the part.

19 Claims, 5 Drawing Sheets

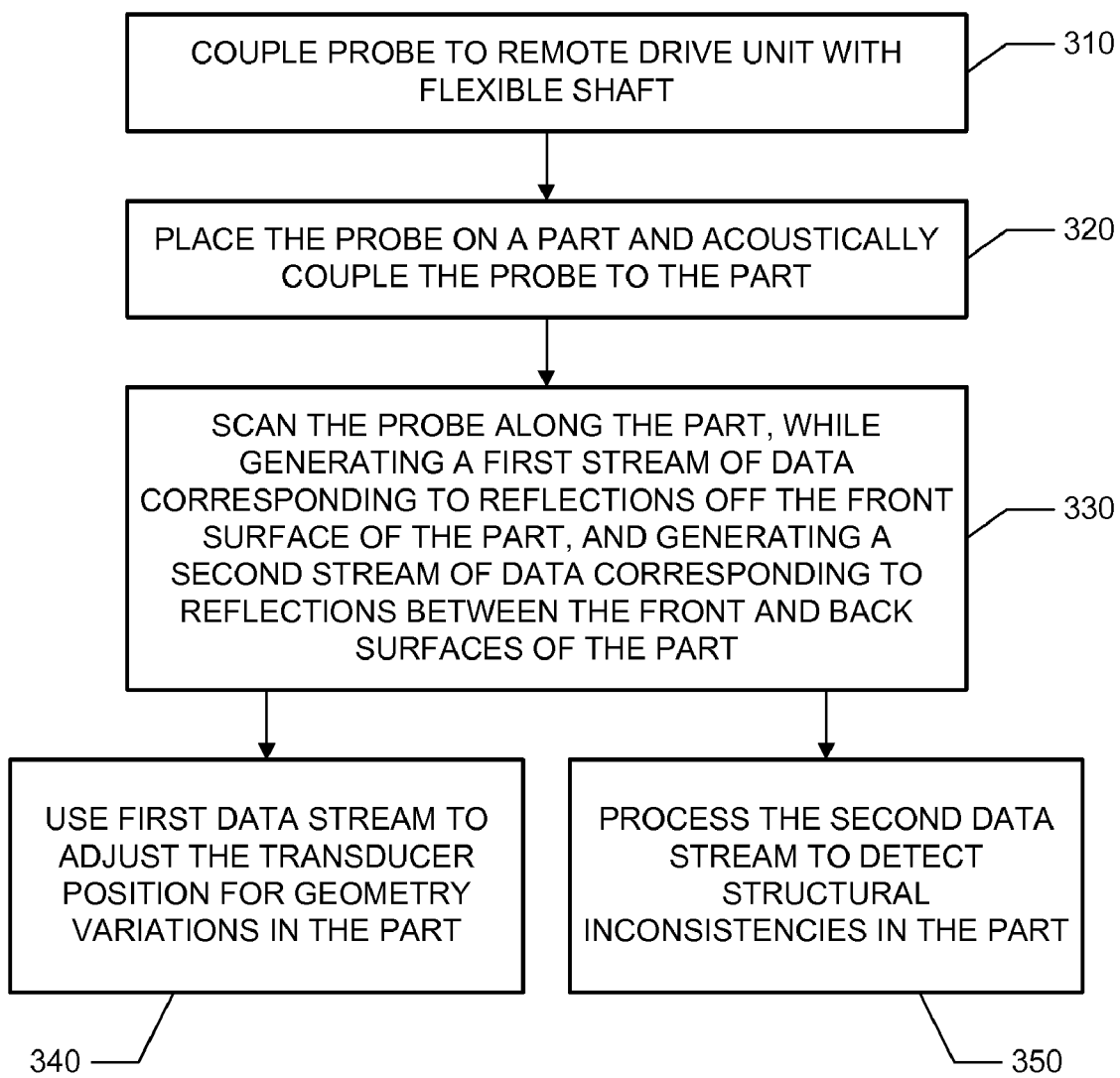

ADJUSTABLE PROBE FOR ULTRASONIC TESTING

BACKGROUND

Nondestructive inspection (NDI) of a structure involves thoroughly examining the structure without harming it or significantly disassembling it. Nondestructive inspection is commonly used in the aircraft industry to validate the health (e.g., integrity and fitness) of aircraft structures.

NDI may be performed on stiffened composite parts of an aircraft. A stiffened part may have flat areas and corners. A corner is referred to as a "corner radius." The stiffened part may be made of a composite material such as carbon fiber reinforced plastic (CFRP). A fuselage stiffener is but one example of a stiffened part.

Structural health of a stiffened part can be determined non-destructively by ultrasonic testing. A corner radius of a stiffened part can be inspected ultrasonically by a probe including a radiused shoe that holds an ultrasonic transducer. During NDI, the shoe's radius is pressed against a corner radius of the part, the transducer is acoustically coupled to the part (e.g., with water), and the shoe is slid along the corner radius. As the shoe is being slid, the transducer operates in pulse/echo mode to generate sound pulses, which are transmitted through the corner radius. Reflected sound pulses indicate whether the corner radius contains a crack, void, delamination, etc.

A problem can arise during NDI of a stiffened part if a corner radius of the part is not formed by concentric inner and outer radii (see, for example inner and outer radii R1 and R2 in FIG. 1). The part might be structurally sound, but a corner radius having non-concentric radii might produce a false negative during NDI. For instance, the inspection might falsely indicate a structural inconsistency such as porosity or delamination.

If a structural inconsistency is indicated, additional testing is performed. If the additional testing reveals a healthy structure, then the time and cost of performing the additional testing was wasted.

False negatives can also significantly slow the flow of production. The time and cost of additional inspection requires the production facility to be "occupied" by the part while undergoing additional testing. This can pose a problem if other parts have to wait for inspection.

Consider aircraft stiffeners. Given the number of features to test on each stiffener, the length of each stiffener, the number of stiffeners in an aircraft, and the number of aircraft being manufactured at any given time, there might be miles of stiffener to inspect. The time and money wasted on false alarms, and the slowdown in production, can be significant.

It would be desirable to reduce the occurrence of false negatives.

SUMMARY

According to an embodiment herein, a system for performing ultrasonic testing on a composite part includes an ultrasonic transducer, a shoe for holding the transducer, and means for automatically adjusting position of the transducer during ultrasonic testing. The transducer position is adjusted to account for geometry variations in the part.

According to another embodiment herein, an ultrasonic probe includes a probe shoe, an ultrasonic transducer carried by the shoe, a mechanism carried by the shoe for adjusting position of the transducer, and at least one flexible shaft coupled to the mechanism for driving the mechanism to adjust the position of the transducer.

According to another embodiment herein, a method of performing nondestructive inspection of a composite part includes coupling a flexible shaft to an adjustment mechanism on an ultrasonic probe, sliding the probe along the part, and receiving pulse/echo data from at least two gates of the probe. The gates focus on reflections from a front surface of the part. The method further includes using the pulse/echo data to drive the shaft to adjust transducer position to correct for geometric variance in the part.

According to another embodiment herein, a method of performing NDI on a composite part includes operating a transducer in pulse/echo mode, collecting a first data stream from at least two gates corresponding to acoustic energy reflected by the front surface of the part, and collecting a second data stream from at least one gate corresponding to any acoustic energy reflected between the front surface and a back surface of the part. The method further includes using the first data stream to automatically adjust position of the transducer so the front surface reflection is relatively flat, and processing the second data stream to determine structural health of the part.

BRIEF DESCRIPTION OF THE DRAWINGS

FIG. 3 is an illustration of a method of using the system of FIG. 2 to perform ultrasonic testing.

DETAILED DESCRIPTION

Figure 1:
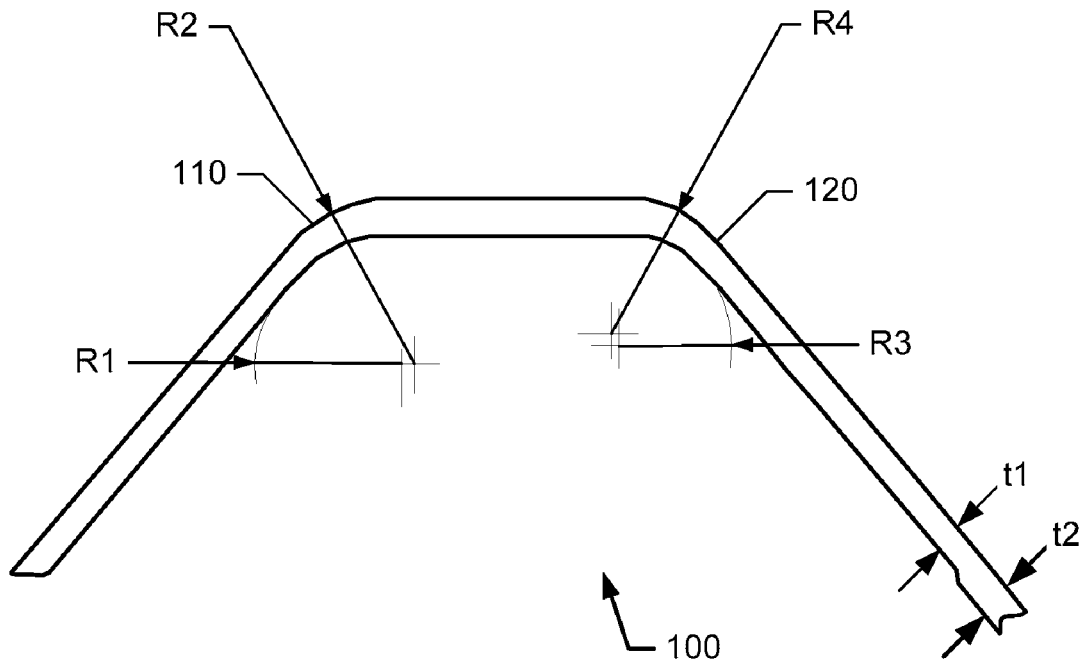
FIG. 1 is an illustration of a composite part having non-concentric corner radii and variable thickness.

Reference is made to FIG. 1, which illustrates a composite part 100 having non-concentric corner radii 110 and 120. The corner radius 110 is non-concentric because its inner and outer radii R1 and R2 don't line up. Similarly, the corner radius 120 is non-concentric because its inner and outer radii R3 and R4 don't line up.

The part 100 also has variable thickness due to a bump in a flat portion. The flat portion has a thickness of t1, and the bump has a thickness of t2. These variances might result from geometric variances in part design (e.g., change in plies) and manufacturing processes.

Figure 2:
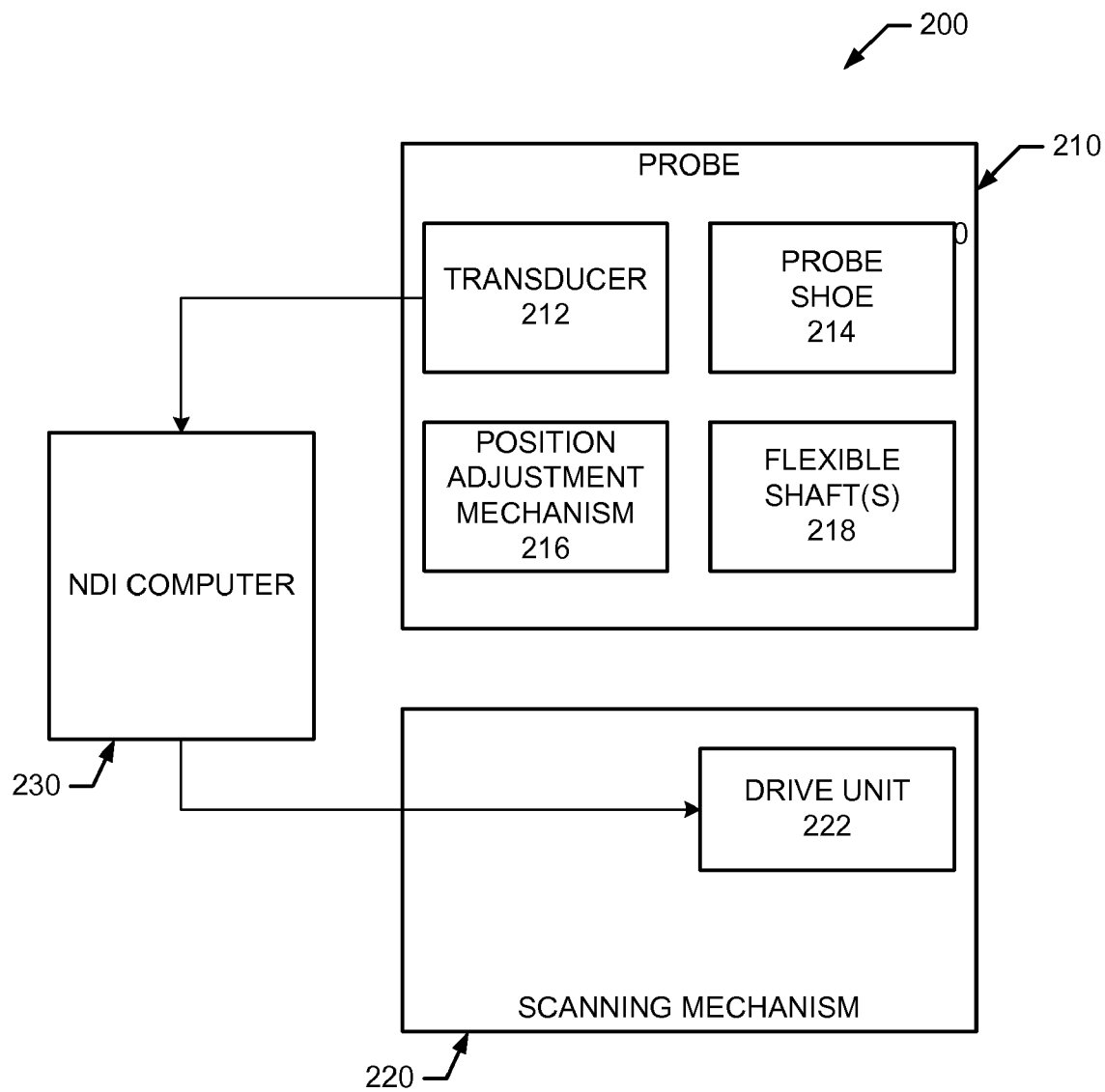
FIG. 2 is an illustration of a system for performing ultrasonic testing.

FIG. 2 illustrates a system 200 for performing nondestructive inspection on a composite part. The system 200 includes a probe 210 having an ultrasonic transducer 212 and a shoe 214 for holding the transducer 212. The shoe 214 is configured to ride along a part.

The system 200 further includes a scanning mechanism 220 for automatically moving the probe 210 along the part. The scanning mechanism 220 may include an end effector and a device (e.g., a robot or gantry) for moving the end effector. The probe 210 may be attached to the end effector.

The system 200 can record position of the transducer during scanning. For example, the system 200 could include an optical encoder (not shown).

The transducer 212 may include an array of discrete transducer elements, and a multi-connector interface. The shoe 214 provides a housing for the array. The array is preferably curved. However, the probe 210 is not so limited to a curved array. In some embodiments, the array may include a combination of a curved section and one or more linear sections. Each section may have a plurality of discrete transducer elements.

The transducer 212 is operable in pulse/echo (PE) mode. Operating in PE mode, the transducer 212 generates sound pulses that are transmitted through the part. Some acoustic energy will be reflected by a front surface of the part, some will be reflected by a back wall of the part, and some acoustic energy might be reflected by any structural inconsistencies between the front and back walls. The transducer 212 also measures the reflected acoustic energy.

The transducer 212 may have multiple time gates. A time gate refers to a window of analysis in time and amplitude. Gates are typically used to filter out data from wedges, front surfaces, etc. A time gate for pulse echo is usually set to find reflections within the part, after the front surface of the part. A gate could be adjusted to look at a particular depth of the part.

Some of the gates are used to detect structural inconsistencies. These gates may analyze only reflections between the front and back surfaces. At least two of the gates are used to detect geometry variations (e.g., non-concentric corner radii and non-uniform thickness) in a part under inspection. These gates may examine the echo only from the front surface of a part. In some embodiments, the gates may provide time of flight (TOF) and amplitude. TOF may use a gate at either the peak value or the first crossing of the signal "higher" in amplitude of the gate threshold (usually in percentage of screen height).

The system 200 further includes an NDI computer 230 for analyzing the TOF and amplitude to locate structural inconsistencies (e.g., porosity, delamination, foreign matter) in a part. The amplitude information indicates whether an anomaly is present. For example, a large reflection, say greater than 40% amplitude, with a linear time corrected gain (TGC) that occurs in time before the back wall reflection, might indicate delamination, foreign material, or another structural inconsistency. The TOF information represents the location of the inconsistency within the material, that is, how far from the surface the inconsistency is located.

The system 200 further includes a means for automatically adjusting position of the transducer 212 as the shoe 214 is riding along the part. The automatic adjustment means may include a position adjustment mechanism 216 and a drive unit 222. The transducer position is automatically adjusted to account for variations in the part. For instance, if the corner radius is non-concentric, the means will adjust the transducer position until a signal indicating a "flat" wave is received (i.e., the signals from the echo from the front surface). If a part's far side is the "tooled" surface, then part thickness changes will decrease the radius in a concave angle part. The transducer would be adjusted accordingly.

The position adjustment mechanism 216 may include a single unit for moving the transducer 212, or it may include separate units for independent control over each axis. An example of a position adjustment mechanism 216 is described below.

By automatically adjusting the transducer position, return signals corresponding to variances are less likely to be identified as structural inconsistencies. Thus, the occurrences of false negatives are reduced. This, in turn, reduces the time and expense wasted on additional testing of false negatives and, consequently, improves production flow.

The drive unit 222 may include one or more electric motors. In some embodiments, the adjustment mechanism 216 and drive unit 222 may all be carried by the probe shoe 214. However, mounting the drive unit 222 on the probe shoe 214 has certain disadvantages. The motors of the drive unit 222 add to the weight that has to be moved by the scanning mechanism 220. Consequently, a larger more expensive robot or gantry is used to move the added weight. At very least, positional accuracy is reduced.

This disadvantage can be avoided by mounting the drive unit 222 on the scanning mechanism 220, and coupling the drive unit 222 to the adjustment mechanism 216 with one or more flexible shafts 218. In some embodiments, the adjustment mechanism 216 is mounted to the probe shoe 216, and the drive unit 222 is mounted to a frame of a gantry.

The flexible shafts 218 should transmit adequate angular motion from the motors to the adjustment mechanism. Adequate transmission will eliminate over shooting the adjustment position of the transducer. The flexible shafts should be small and compatible with the motors. The flexible shafts 218 should be made of a material that is corrosion-resistant. Examples of materials for the shafts 218 include, but are not limited to, stainless steel and plastic.

The drive unit 222 may be controlled by the NDI computer 230. In other embodiments, the drive unit 222 may have its own dedicated controller. The communications between the NDI computer 230 and the probe 210 and scanning mechanism 220 may be made over cable connections. In some embodiments, the communications may be performed over a network, whereby the NDI computer 230 may be located remotely from the probe 210 and scanning mechanism 220.

Reference is now made to FIG. 3, which illustrates a method of using the system 200 to perform NDI on a part. The probe 210 may be configured to inspect the entire part during a single scan, or it may be configured to inspect a portion of the part during a single scan. The probe 210 may be configured to inspect only a corner radius of the part, or only a flat portion of the part.

At block 310, if the drive unit 222 and the adjustment mechanism 216 are mounted to different structures, they are coupled together. For example, the drive unit 222 may be connected to the adjustment mechanism 216 by one or more flexible shafts 218.

At block 320, the probe 210 is placed on the part and acoustically coupled to the part. In some embodiments, the part and probe 216 may be immersed in water. In other embodiments, the part could be coupled to the probe 216 by an ultrasonic gel or an impedance matching "wedge" material.

At block 330, the probe 210 is scanned along the part. As the probe 210 is scanned along the part, its ultrasonic transducer generates acoustic signals and detects reflections of the signals. Gates of the probe 210 provide first and second streams of pulse/echo data. In some embodiments, the pulse echo data may be made available on as an analog output.

The first stream of pulse/echo data will be used to adjust the transducer position for geometry variations in the part. The first stream of data corresponds to reflections off the front surface of the part. For example, the analog output from two (A and B) gates may include A% and B%, which are peak amplitude value in the A and B gates respectively. Thickness may be defined as TOF of the amplitudes, but in some embodiments may be defined as B peak in gate B minus the edge of A in gate A. That is, thickness=B%−A%.

At block 340, as the probe 210 is scanned along the part, the first stream of data is used to adjust the transducer position to compensate for geometric variance in the part. The NDI computer 230 or a dedicated controller on the drive unit 220 may use the first stream as illustrated in FIG. 4.

At block 350, the second stream of data is used to determine whether the part has any structural inconsistencies. The second stream of data may correspond to reflections between the front and back surfaces of the part. The NDI computer 230 may process the second data stream as the probe 210 is scanned along the part, or it may process the second stream off-line, after the scanning has been completed.

Figure 4:
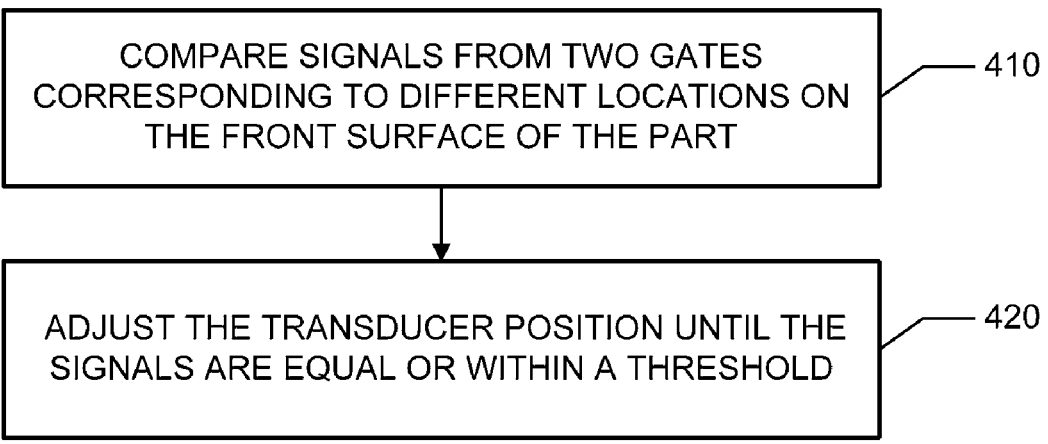
FIG. 4 is an illustration of a method of using data generated by the system of FIG. 2 to account for geometry variations in a part during ultrasonic testing.

Reference is now made to FIG. 4, which illustrates a method of processing the first data stream. In the embodiment of FIG. 4, two gates A and B provide pulse/echo data. In other embodiments, more than two gates may be used.

At block 410, signals provided by two gates (e.g., the A and B gates) are compared. The two gates correspond to different locations on the front surface of the part.

At block 420, the transducer position is adjusted until the signals (amplitudes and/or TOF) are equal or within a threshold. The comparison of signals may produce an error signal, which the drive unit uses to drive the position adjustment mechanism.

The method of FIG. 4 can also adjust the transducer position to minimize the loss of signal due to Snell's Law. By keeping the signal perpendicular to the surface of the part, maximum energy is transmitted into the part.

Figure 5:
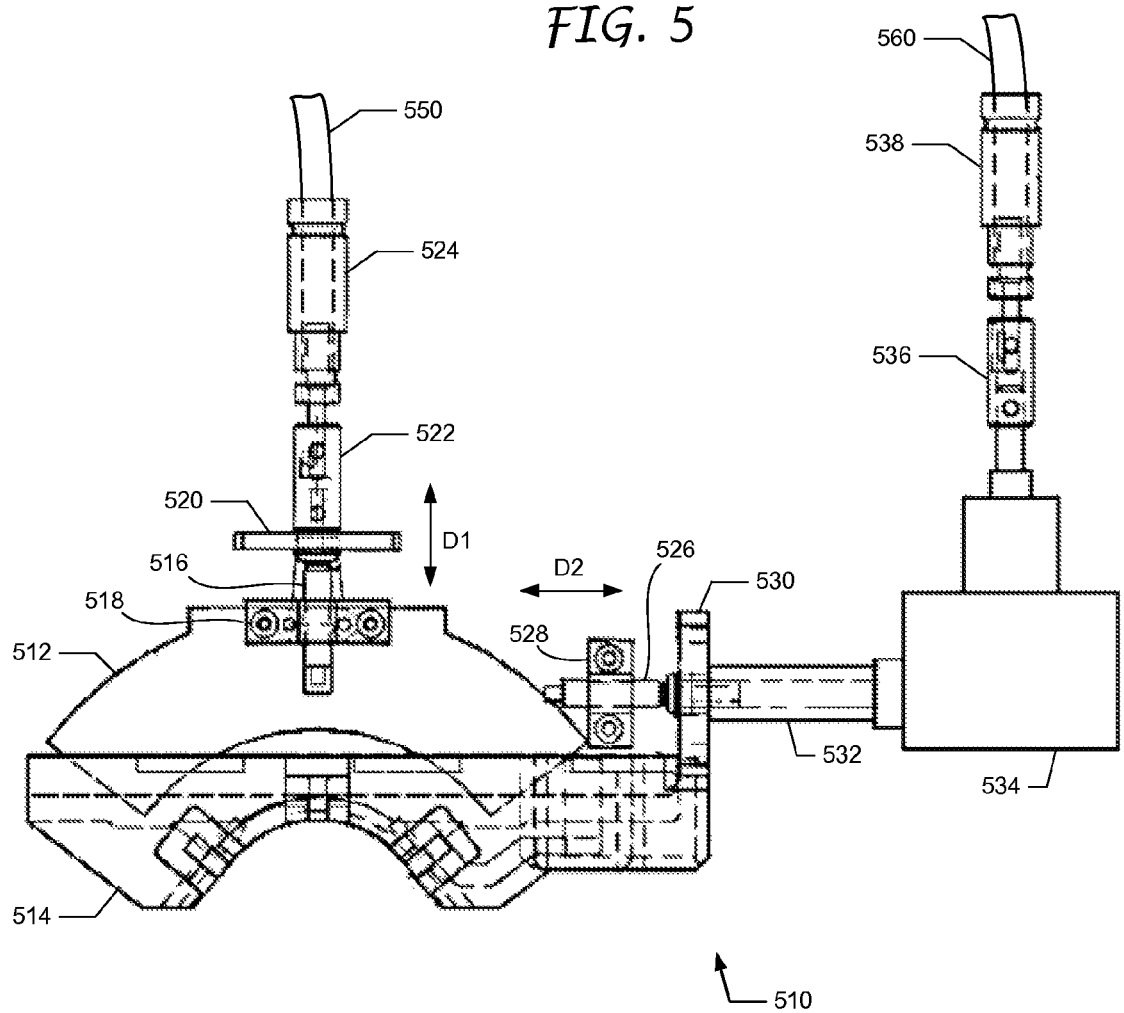
FIG. 5 is an illustration of an ultrasonic probe and flexible shafts.

Reference is now made to FIG. 5, which illustrates an example of a probe 510. The probe 510 includes a curved transducer array 512, and a shoe that provides a housing 514 for the transducer array. The housing 514 may include an upper half and a lower half (the upper half has been removed for clarity). The upper housing may hold the transducer array 512. Different size lower housings can be fitted into the shoe to minimize the amount of water needed to couple the sound through the part.

The probe 510 further includes a first lead screw 516, lead screw slider 518 and flange bearing 520 for adjusting the transducer array 512 in a first direction (D1). A first flexible cable 550 is coupled to the first lead screw 516 by a first shaft coupling 522. A first cover 524 is provided for the first flexible cable 550.

The probe 510 further includes a second lead screw 526, lead screw slider 528, and flange bearing 530 for adjusting the transducer array 512 in a second direction (D2). A second flexible cable 560 is coupled to the second lead screw 526 by a coupling 532, miter gearbox 534, and second shaft coupling 536. A second cover 538 is provided for the first flexible cable 550.

An ultrasonic transducer cable (not shown) provides a data path from the transducer to the NDI computer. The first flexible cable 550 is connected to a first electric motor (not shown), and the second flexible cable 560 is connected to a second electric motor. The electric motors are driven independently to move the transducer array 512 in the first and second directions (D1 and D2). Each electric motor may include an encoder (not shown) for determining shaft position or rotation.

Ultrasonic testing as described herein is not limited to a part having any particular composition. However, the ultrasonic testing is especially useful for testing parts made of composite material. Examples of composite material include, but are not limited to, Graphite Epoxy, Resin Infusion, and hybrid materials (e.g., Graphite/Ti).

The ultrasonic testing is not limited to any particular type of part. However, it is especially advantageous for performing comprehensive, yet relatively fast testing of composite components that make up aircraft wings and fuselages (e.g., fuselage stiffeners).

Figure 6A:
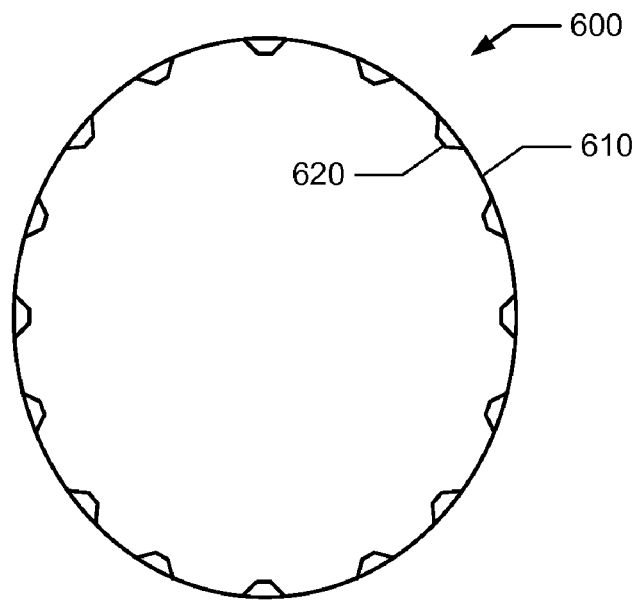
FIGS. 6a and 6b are illustrations of a fuselage barrel and a hat stiffener for the barrel.

Reference is made to FIG. 6a, which illustrates a portion of an aircraft fuselage 600. The fuselage 600 includes skin 610 and a plurality of fuselage stiffeners 620 disposed about the skin 610. The fuselage stiffeners 620 increase the stiffness of the skin 610. The skin 610 and the fuselage stiffeners 620 may be made of a composite such as carbon fiber reinforced plastic (CFRP).

The number of fuselage stiffeners 620 shown in FIG. 6a is for illustrative purposes only. The number of fuselage stiffeners 620 in a fuselage 600 will be aircraft-specific. For example, certain large commercial aircraft could have about eighty fuselage stiffeners 620 per barrel.

Figure 6B:
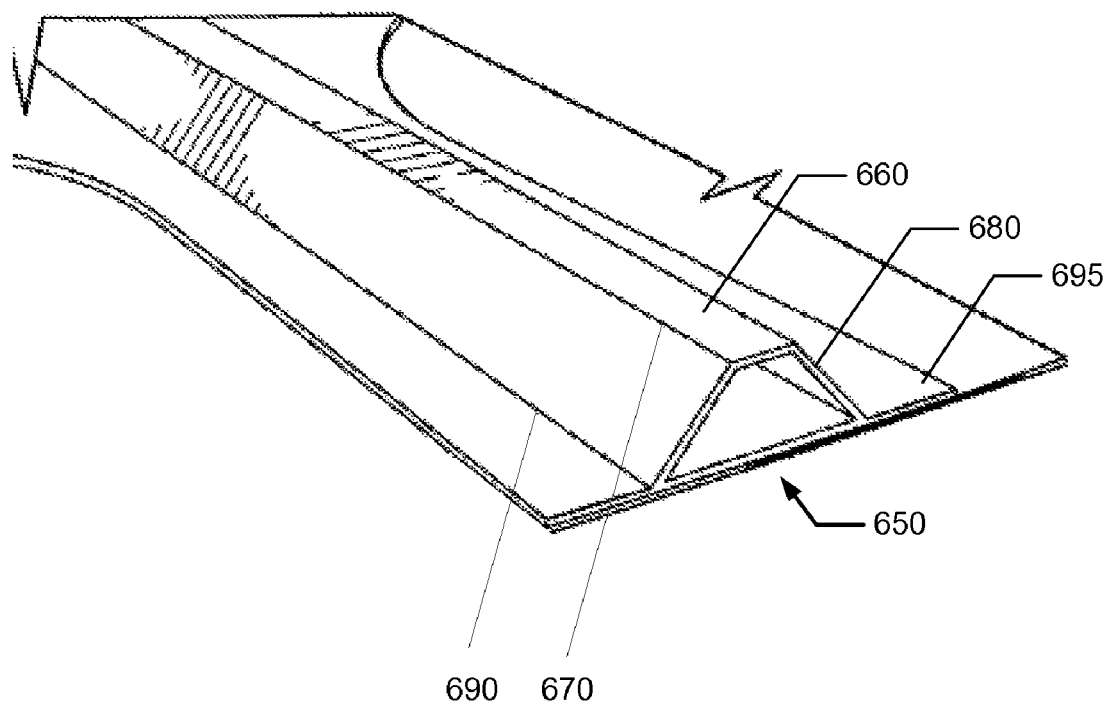

Additional reference is made to FIG. 6b, which illustrates a certain type of fuselage stiffener that will be referred to as a "hat stiffener" 650. The hat stiffener 650 includes an upper cap 660, upper radii 670, upper webs 680, lower radii 690, and lower webs 695.

A hat stiffener 650 may be inspected according to a method described herein. In some embodiments, a method herein may be used to perform comprehensive testing of the hat stiffener 650. Comprehensive testing would include ultrasonic testing of all features 660-695 of the hat stiffener 650. In other embodiments, ultrasonic testing may be performed on only the cap 660 and upper radii 670.

The hat stiffeners 650 of a fuselage may be inspected at different stages of aircraft construction. As a first example, the hat stiffeners 650 are inspected after being fastened to (e.g., co-cured with) the fuselage skin 610. For instance, the inspection could be performed on a fuselage barrel after it comes out of the autoclave, but before it is removed from the fabrication assembly fixture[s]. The inspection is performed before any frames and beams are added. Thus, the method may be performed by the supplier of the barrel section.

As a second example, the hat stiffeners 650 may be inspected before they are fastened to the fuselage skin 610. Ultrasonic probes as described herein may be moved along the hat stiffeners 650 by a feed through system, or the probes could be attached to a scanning table.

The invention claimed is:

1. A system for performing ultrasonic testing on a composite part, the system comprising:
   an ultrasonic transducer;
   a shoe for holding the transducer; and
   means for automatically adjusting position of the transducer during ultrasonic testing;
   wherein the transducer provides first and second streams of data during testing, the first stream used by the means to correct the position of the transducer for geometry variations in the part, the second stream used to detect structural inconsistencies in the part.

2. The system of claim 1, wherein the geometry variations include non-concentric corner radii.

3. The system of claim 1, wherein the geometry variations include variations in thickness in the part.

4. The system of claim 1, wherein the means includes a mechanism carried by the shoe for adjusting transducer position, a drive unit not carried by the shoe; and at least one flexible shaft for mechanically coupling the mechanism to the drive unit.

5. The system of claim 4, further comprising a scanning mechanism for scanning the probe along the part, the drive unit mounted to the scanning mechanism.

6. The system of claim 1, wherein the first stream includes information from at least two gates of the probe, the information about acoustic reflections from different locations on the front surface of the part.

7. The system of claim 6, wherein signals from first and second gates are compared, and wherein the transducer position is adjusted until the signals are about equal.

8. The system of claim 6, wherein the second stream includes information from additional gates of the probe.

9. The probe of claim 1, wherein the mechanism includes a first lead screw assembly for adjusting the transducer array in a first direction, a second lead screw assembly for adjusting the transducer array in a second direction, and first and second flexible shafts coupled to the first and second lead screws.

10. The probe of claim 1, wherein the shoe includes an upper housing for holding the transducer and lower housings of different sizes that can be fitted into the shoe to minimize the amount of water needed to couple sound through the part.

11. A method of performing nondestructive inspection of a composite part, the method comprising:
coupling a flexible shaft to an adjustment mechanism on an ultrasonic probe;
sliding the probe along the part, while using the flexible shaft to transmit angular motion from motor to the adjustment mechanism;
receiving pulse/echo data from at least two gates of the probe, the gates focusing on reflections from a front surface of the part; and
using the pulse/echo data to control the motion of the shaft to adjust transducer position to correct for geometric variance in the part.

12. The method of claim 11, wherein signals from first and second gates are compared, and wherein the transducer position is adjusted until the signals are about equal.

13. The method of claim 11, further comprising processing additional pulse/echo data from additional gates of the probe to detect any structural inconsistencies in the part.

14. The method of claim 11, wherein the part is a hat stiffener, and wherein pulse echo testing is performed only on a cap and upper radius of the hat stiffener.

15. A method of performing NDI on a composite part comprising:
operating a transducer in pulse/echo mode;
collecting a first data stream from at least two gates corresponding to a acoustic energy reflected by the front surface of the part, and collecting a second data stream from at least one gate corresponding to any acoustic energy reflected between the front surface and a back surface of the part;
using the first data stream to automatically adjust position of the transducer so the front surface reflection is relatively flat; and
processing the second data stream to determine structural health of the part.

16. The method of claim 15, wherein signals from first and second gates are compared, and wherein the transducer position is adjusted until the signals are about equal.

17. The method of claim 16, wherein the transducer position is adjusted by an adjustment mechanism and drive unit; and wherein the drive unit drives the adjustment mechanism in response to the comparison of amplitudes.

18. The method of claim 16, wherein the adjustment mechanism is carried by the probe and wherein the drive unit is not carried by the probe; and wherein the method further comprises mechanically coupling at least one flexible shaft between the adjustment mechanism and the drive unit.

19. The method of claim 15, wherein the part is a hat stiffener, and wherein pulse echo testing is performed only on a cap and upper radius of the hat stiffener.

\* \* \* \* \*